United States Patent [19]
Guidotti et al.

[11] Patent Number: 5,741,241
[45] Date of Patent: Apr. 21, 1998

[54] ABSORBENT BODY FOR AN ABSORBENT ARTICLE

[75] Inventors: Ted Guidotti, Göteborg; Eje Österdahl, Västra Frölunda, both of Sweden

[73] Assignee: SCA Mölnlycke AB, Gothenburg, Sweden

[21] Appl. No.: 318,771

[22] PCT Filed: Apr. 21, 1993

[86] PCT No.: PCT/SE93/00348

§ 371 Date: Oct. 14, 1994

§ 102(e) Date: Oct. 14, 1994

[87] PCT Pub. No.: WO93/21882

PCT Pub. Date: Nov. 11, 1993

[30] Foreign Application Priority Data

Apr. 28, 1992 [SE] Sweden ................................. 9201333

[51] Int. Cl.[6] .................................................. A61F 13/15
[52] U.S. Cl. ........................ 604/368; 604/378; 604/375
[58] Field of Search ................................ 604/358, 375, 604/378, 372, 385.1, 381, 368, 367

[56] References Cited

U.S. PATENT DOCUMENTS

| | | | |
|---|---|---|---|
| 4,500,315 | 2/1985 | Pieniak et al. | |
| 4,652,484 | 3/1987 | Shiba et al. | 604/372 |
| 5,019,063 | 5/1991 | Marsan et al. | 604/378 |
| 5,134,007 | 7/1992 | Reising et al. | 604/385.1 |
| 5,236,427 | 8/1993 | Hamajima et al. | 604/378 |
| 5,304,161 | 4/1994 | Noel et al. | 604/378 |
| 5,423,787 | 6/1995 | Kjellberg | 604/378 |

FOREIGN PATENT DOCUMENTS

| | | |
|---|---|---|
| 0401189 | 5/1990 | European Pat. Off. . |
| 136432 | 9/1965 | New Zealand . |
| 178422 | 1/1992 | Norway . |
| 178603 | 10/1992 | Norway . |
| 463747 | 8/1991 | Sweden . |
| 465553 | 9/1991 | Sweden . |
| 9111978 | 8/1991 | WIPO . |
| WO/9111161 | 9/1991 | WIPO . |
| WO 91/14415 | 10/1991 | WIPO . |

*Primary Examiner*—Mary Beth Jones
*Assistant Examiner*—David J. Cho
*Attorney, Agent, or Firm*—Burns, Doane, Swecker & Mathis LLP

[57] ABSTRACT

An absorbent body intended to form the absorbent element of an absorbent article, such as a diaper, an incontinence guard or a sanitary napkin, includes a first fibre-based absorbent layer which lies proximal to the wearer in use, and a second, fibre-based absorbent layer which is intended to lie distal from the wearer in use, this second layer having a high liquid-dispersing ability. An absorbent body exhibiting particularly good absorption properties has been obtained by including in the first layer (16) a superabsorbent material (18) of high gel-strength and by mixing this superabsorbent essentially uniformly in the fibre material within at least one area of the layer, and by including between the fibre layers (17a, 17b) of the second layer (17) a layer (20) of superabsorbent material.

20 Claims, 1 Drawing Sheet

5,741,241

ABSORBENT BODY FOR AN ABSORBENT ARTICLE

TECHNICAL FIELD

The present invention relates to an absorbent body which is intended to form the absorbent element of an absorbent article, such as a diaper, an incontinence guard or a sanitary napkin, and includes a first absorbent layer which is based on cellulose fluff-pulp and which is intended to face towards the wearer in use, i.e to lie proximal to the wearer, and a second absorbent layer which is also based on cellulose fluff-pulp and which is intended to lie distal from the wearer in use, i.e. to face away from the wearer, and which has a high liquid-dispersion capability.

BACKGROUND OF THE INVENTION

An absorbent body, or pad, intended for absorbent articles such as disposable diapers, sanitary napkins and incontinence guards is normally formed of one or more layers of cellulose fluff-pulp and often contains so-called superabsorbents, which are polymers that are capable of absorbing several times their own weight of water or body liquid. The absorbent body may also include other constituents, for instance constituents which improve its liquid-dispersing properties or which increase its ability to hold together and its ability to resist deformation in use.

One serious problem, primarily encountered with diapers and incontinence guards which are intended to receive and absorb relatively large quantities of liquid, is that the articles often begin to leak before their total absorption capacity has been utilized to the full.

Although the use of superabsorbents in absorbent bodies will impart thereto a high absorption capacity and also improve their ability to retain the liquid absorbed, even when the absorbent body is subjected to external pressure forces, present-day superabsorbents have a low absorption rate. Since urination often results in the discharge of large quantities of liquid in the course of some few seconds, the absorbent body will often become temporarily saturated with liquid in local areas, such that further urine discharged by the wearer will leak from the absorbent body.

This premature leakage is, of course, highly irritating to the wearer and also to his/her medic.

Another problem encountered with absorbent sanitary articles of the aforedescribed kind is one of keeping the surface of the article which lies against the wearer in use as dry as possible during the whole of its use period and to prevent so-called rewetting, i.e. to prevent liquid that has already been absorbed being pressed back out of the absorbent pad and rewetting the wearer's skin or giving rise to leakage. The rewetting properties of an absorbent article are improved to some extent when the absorbent body includes superabsorbents which bind the absorbed liquid chemically, even when the article is subjected to external pressure, for instance when the user sits down. However, one difficulty in this regard is in constructing the absorbent body in a manner which will enable the liquid to spread within the absorbent body and reach the superabsorbent material.

Swedish Patent Application No. 9100274-1 describes an absorbent body which includes at least two different cellulose fluff-pulps, wherein the fibre structure of the first absorbent layer is comprised chiefly of a first type of fluff-pulp having an open fibre structure and a low liquid-dispersing capability and a critical bulk which exceeds 8 $cm^3/g$ at 2.5 kPa, whereas the fibre structure of the second absorbent layer is comprised chiefly of a second type of fluff-pulp having a critical bulk which is beneath 8 $cm^3/g$ at 2.5 kPa and having a higher liquid-dispersing capability than the fluff-pulp in the first absorbent layer.

As a result of its open fibre structure, the first absorbent layer is able to accommodate a large amount of liquid between its fibres and is therefore able to receive large quantities of liquid over a short period of time, i.e. has a high instantaneous liquid-absorption capability.

The second absorbent layer, which has a higher liquid-dispersing capability than the first absorbent layer, is able to drain liquid from the first layer and spread the liquid through the second layer.

It is also proposed that the second absorbent layer and possibly also the first absorbent layer shall include a superabsorbent material and it is suggested that this material is admixed essentially uniformly in the fluff-pulp within at least one region of the layer. In this way, there has been produced an absorbent body which has a high instantaneous absorption capacity and the ability to counteract rewetting of the wearer's skin by the liquid already absorbed.

Hitherto, an absorbent body in which superabsorbents have been admixed generally uniformly in the fluff-pulp and the absorbent body then compressed has normally been considered to provide the best absorption properties, see for instance EP-B-0 122 042.

SUMMARY AND OBJECTS

An object of the present invention is to provide an absorbent body of the kind defined in the introduction which possesses further improved absorption properties. This object has been achieved with an absorbent body in which the first layer includes a superabsorbent material of high gel-strength which is admixed essentially uniformly in the fluff-pulp within at least one area of the layer, and in which the second layer includes at least one layer of superabsorbent material.

By admixing a superabsorbent material of high gel-strength in the first layer of the absorbent body, the layer will retain its open fibre structure even when the superabsorbent becomes wet and swells. Thus, instead of expanding so as to block the pores of the capillary system when becoming wet, the superabsorbent will push the fibres apart as it expands, so that the pores in the capillary system will also expand. As a result, further liquid delivered to the absorbent body will be readily taken-up by the fibre structure in the first layer.

The superabsorbent material in the second layer of the absorbent body is applied in the form of a layer instead of in admixture with the fibres as in the case of the first layer. It has surprisingly been found that this results in improved liquid dispersion, improved coherency and improved absorption rate in the second layer. The superabsorbent material in the second layer will preferably also have a high gel-strength, so that optimum liquid-dispersion properties are obtained.

The rate of absorption of a cellulose body which has superabsorbent material mixed therein will be lower than a cellulose body which contains no superabsorbent. This is essential in order for the first layer to function as a liquid-receiving layer which is able to receive large quantities of liquid.

On the other hand, when a layer of superabsorbent material is placed between cellulose layers, the dispersion properties of the purely cellulose body are retained and the liquid is therefore able to reach the superabsorbent material distributed in the second layer more easily, this second layer functioning as a liquid-dispersion layer.

Further features of the invention and advantages afforded thereby will be evident from the depending Claims and from the following description.

BRIEF DESCRIPTION OF THE DRAWINGS

The invention will now be described in more detail with reference to exemplifying embodiments thereof and also with reference to the accompanying drawings.

DESCRIPTION OF EMBODIMENTS

Figure 1:
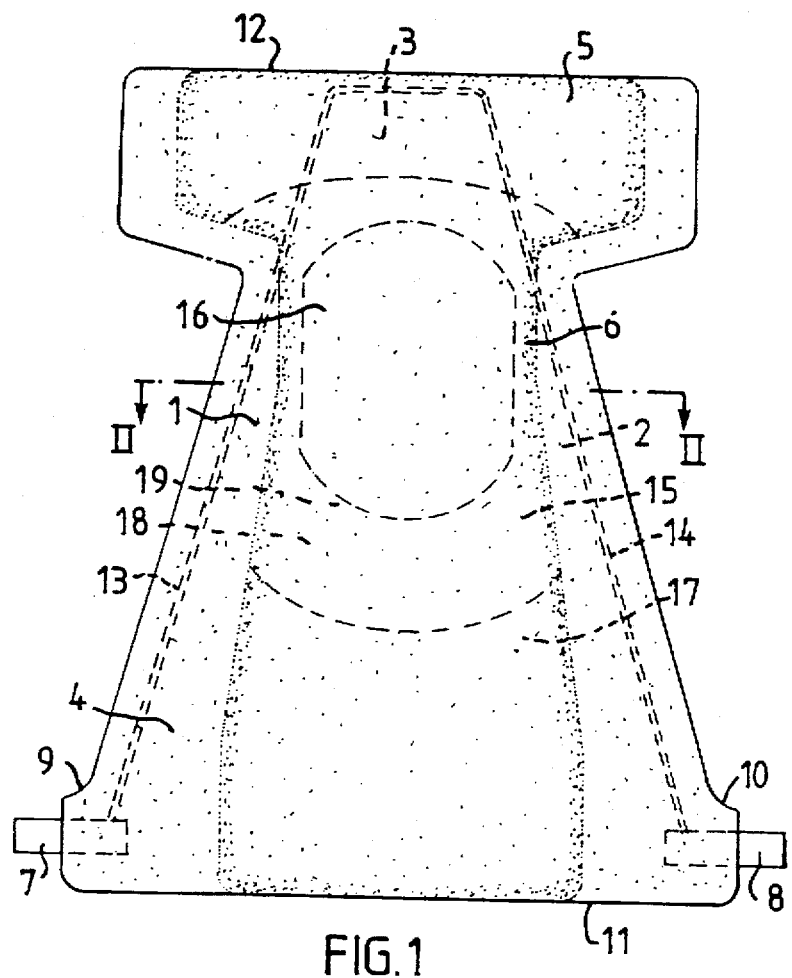
FIG. 1 is a top view of a diaper as seen from the side which lies proximal to the wearer in use.
Figure 2:
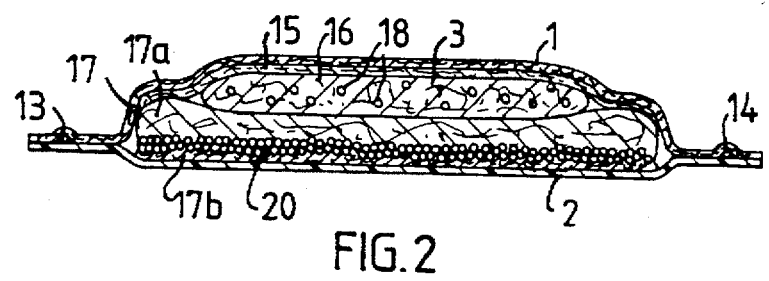
FIG. 2 is a sectional view taken on the line II—II in FIG. 2.

The diaper illustrated in FIG. 1 is comprised of a liquid-permeable casing sheet 1, for instance a non-woven or perforated plastic film, a liquid-impermeable casing sheet 2, for instance a plastic film or a hydrophobic non-woven material, and an absorbent body 3 enclosed between the two layers 1, 2.

The diaper is intended to embrace the lower part of the wearer's trunk, in the manner of a pair of absorbent underpants. To this end, the diaper is provided with a back part 4 which, when the diaper is worn, will be located rearwardly on the wearer, a front part 5 which, when the diaper is worn, will be located forwardly on the wearer, and a narrower crotch part 6 which extends between the back part 4 and the front part 5 of the diaper and which, when the diaper is worn, is located in the crotch region of the wearer, between the thighs thereof. Fastener taps 7, 8 are provided on the side edges 9, 10 of the back part 4 extending in the longitudinal direction of the diaper, close to the rear waist edge 11 of said diaper, so as to enable the diaper to be secured in the desired pants-like form. When the diaper is to be used, the fastener tabs 7, 8 are fastened to the outer surface of the front diaper part 5, close to the forward waist edge 12, thereby holding the diaper together around the wearer's waist.

The diaper illustrated in FIG. 1 also includes pre-stretched elastic devices 13, 14 which extend over the diaper in a V-shaped pattern, with the apex of the V located on the forward waist edge 12 of the diaper. The elastic devices 13, 14 may consist of any suitable material, such as elastic foam, elastic bands or covered elastic threads. For the sake of convenience, the elastic devices 13, 14 have been shown in a stretched state. However, as soon as the tension is removed, the elastic devices will contract and therewith form elastic leg openings on the diaper.

The absorbent body 3 is comprised of a number of mutually different layers. Nearest to the liquid-permeable casing sheet 1 is a thin cellulose fluff-pulp layer 15 of high critical bulk, large pore volume and low liquid-dispersion ability. By critical bulk is meant the bulk at which a cellulose body will neither collapse nor expand when becoming wet. A cellulose fluff-pulp of high critical bulk will retain an open structure of large pore volume even when wet.

Seen in a direction towards the liquid-impermeable casing sheet 2, there then follows a first absorbent layer 16 which is comprised of cellulose fluff-pulp of large pore volume, high wet resiliency and low liquid-dispersion ability, and a second absorbent layer 17 comprised of cellulose fluff-pulp of low pore volume, low wet resiliency and high liquid-dispersion ability. Both absorbent layers also include super-absorbent material.

The cellulose fluff-pulp layer 15 lying closest to the liquid-permeable casing layer 1, and also the second absorbent layer 17 have a T-configuration with the cross-member of the T being located at the front diaper part 5. The first absorbent layer 16, on the other hand, has an oval shape and is located generally in the crotch part 6 of the diaper, around the so-called wetting point.

It will be understood that the illustrated and described diaper is merely intended to exemplify the invention and shall not be considered to limit the scope of the invention. For instance, the shape of the diaper and its construction in other respects may be varied. Similarly, the first absorbent layer 16 may full cover the second absorbent layer. Furthermore, the thin cellulose fluff-pulp layer 15 located nearest the liquid-permeable casing layer 1 can be omitted.

The wetting point is that area of the diaper surface onto which the discharged body liquid first comes into contact. As will be understood, it is not possible in practice to establish any specific point or area in this regard, although it can be generally accepted that the body liquid will be delivered to the diaper within a given, limited area thereof. In general, this area is displaced slightly towards the front diaper part, in the case of both men and women wearers. Since the dispersion of the liquid in the first absorbent layer 16 is only slight, it is sufficient for this layer to cover solely the area of the diaper in which wetting is most likely to occur.

The first absorbent layer 16 thus functions as a receiving area for discharged body liquid. Because the fibre structure in this layer is porous, the liquid is able to quickly penetrate into the layer 16 and be collected thereby.

A chemi-thermo mechanical cellulose fluff-pulp, so-called CTMP, has generally a greater pore volume, higher wet-stability and lower liquid-dispersing ability than a chemically manufactured fluff-pulp. The fact that the fluff-pulp has a large pore volume signifies that the capillaries between the fibres are coarse, which is naturally one reason why the liquid-dispersing ability is low, since this ability reduces with increasing capillary sizes. The liquid-dispersing ability of the fluff-pulp and its affinity to liquid is also due to the fact that the wood substances that remain in the fluff-pulp impart to the fibres of CTMP-pulp other surface properties than the fibres of chemical pulps.

One reason for the high wet-stability of the CTMP-pulps is because they contain relatively thick or coarse fibres having a fibre weight between 180 and 600 mg/km. Furthermore, CTMP-pulp contains lignin, which functions as a cellulose-fibre stiffening element. Since lignin retains its structure even when wet, fibres which have a high lignin content are relatively rigid, even in a wet state. Consequently, a fibre layer which is comprised substantially of such fibres will have good wet-stability and a high critical bulk, above 8 $cm^3/g$ at 2.5 kPa.

Consequently, CTMP fluff-pulp is suitable for use in the first absorbent layer 16. This layer may consist entirely, or at least to a substantial part, of CTMP fluff-pulp or some other fluff-pulp which has similar properties, e.g. Southern pine. It is also conceivable to use chemical pulp in the first absorbent layer 16, despite the high liquid-dispersing capacity of the chemical pulp, since this capacity is lowered when superabsorbent material is admixed with the pulp. Naturally, absorbent materials other than fluff-pulp are conceivable, such as synthetic fibres or mixtures of synthetic fibres and fluff-pulp.

The first absorbent layer 16 contains between 2 and 30%, preferably between 2 and 15%, superabsorbent 18, calculated on the total dry weight of the layer in that area in which the superabsorbent is mixed. The superabsorbent is distributed generally uniformly in the layer, within at least one area or region thereof, and is intended to absorb and to bind any liquid that remains in the layer, even after the layer has been drained by the second absorbent layer 17. Because the first absorbent layer 16 includes superabsorbents, there is obtained a very dry surface, since the fibre interspaces in the layer are emptied of liquid practically completely.

As before mentioned, the superabsorbent 18 in the first absorbent layer shall have a high gel-strength, so that the layer will retain an open fibre structure even when becoming wet.

The second absorbent layer 17 also contains superabsorbent material, in this case in the form of one or more layers 20 of flakes, fibres, granules, powder or the like. This layer 20 extends either over the whole of the absorbent layer 17 or is restricted to at least one area thereof. This area 19 may, for instance, be slightly larger than the first absorbent layer 16 and, similar to said layer, may be limited essentially to the crotch part of the diaper.

The proportion of superabsorbent included in the second absorbent layer 17 will preferably be between 2 and 60%, preferably between 10 and 50%, calculated on the total dry weight of the layer.

The superabsorbent in the second absorbent layer 17 will preferably have a high gel-strength, i.e. has the ability to swell substantially unaffected by normal occurring pressure forces, so as not to block and impede dispersion of the liquid. Characteristic of these superabsorbents is that they have a high degree of cross-linking which renders them more difficult to compress in comparison with a gel that has a lower degree of cross-linking.

Other important properties of the superabsorbents suitable for use with the present invention are high absorbency under pressure and a high absorption rate.

The fluff-pulp in at least the layer 17a of the second absorbent layer 17 which is proximal to, or faces towards, the first absorbent layer 16 will preferably be comprised substantially of fluff-pulp or some other absorbent material having a high liquid-dispersion capability. Chemically produced fluff-pulps generally have good liquid-dispersing capability. Since chemical fluff-pulps are chiefly comprised of solely cellulose material, the fine fibres have a weight of 140–190 mg/km, a low degree of stiffness and low wet-stability, and a critical bulk beneath 8 cm³/g at 2.5 kPa. A fibre structure which is comprised chiefly of chemically produced cellulose fluff-pulp will have a large number of fibres per unit volume, which provides a dense structure with fine capillaries. When such a fibre structure becomes wet, the fibre structure collapses because of the low wet-rigidity of the fibres and forms a structure which has a relatively low absorption capacity but a high liquid-dispersing capacity. At least 60% of the layer 17a may comprise a chemical fluff-pulp.

Because, in accordance with the preferred embodiment, there is a difference in capillary size between the fluff-pulps in the first absorbent layer 16 and the fluff-pulp layer 17a of the second absorbent layer 17, said layer 17a lying proximal to the first absorbent layer 16, liquid is actively transported from the layer 16 to the layer 17, since the capillary forces constantly act to transport liquid in a direction away from the coarser capillaries to the finer capillaries. These capillary differences also counteract rewetting of the skin by liquid that has already been absorbed in the second absorbent layer 17.

Thus, discharged body liquid is first collected in the first absorbent layer 16, which functions as a buffer or reservoir, this layer being successively drained as the second absorbent layer 17 absorbs and disperses liquid.

The second fluff-pulp layer 17b in the second absorbent layer 17 may consist of a chosen fluff-pulp, for instance CTMP-pulp or chemical pulp.

When forming the second absorbent layer 17, there is preferably used a suction drum whose outer cylindrical surface is provided with forming recesses. The drum interior is placed under vacuum conditions and the bottom surfaces of the forming recesses have a sieve-like configuration. The second absorbent layer 17 is formed in three stages. In a first stage, airborne pulp fibres are delivered to the forming recesses and the resultant layer is compressed to some extent by the vacuum prevailing in the drum. In a second step, superabsorbent material is strewn over the pulp layer. The vacuum is discontinued in this second stage, so that the pulp fibres will loosen from one another to some extent and therewith allow the superabsorbent particles to penetrate slightly in between the fibres. This results in a better bond between pulp layer and superabsorbent layer. In a third stage, a layer of pulp is formed over the layer of superabsorbent and the absorbent layer 17 is compressed to some extent with the aid of a vacuum, prior to said layer being placed together with the first absorbent layer 16, whereafter the layers are finally compressed.

Comparison tests have been carried out between an inventive absorbent body and an absorbent body in which the superabsorbent was mixed generally homogeneously with the fluff-pulp fibres in both absorbent layers.

EXAMPLE 1

Rewetting

Rewetting was tested for two fluff-bodies A and B, each comprised of two absorbent layers, an upper layer comprised of a softwood-type CTMP-pulp and a lower layer comprised of chemical softwood pulp. The upper absorbent layer of body A had a surface weight of 350 g/m² and contained 1.2 g superabsorbent which was mixed generally homogeneously with the fluff-pulp fibres. The lower absorbent layer of body A was comprised of two fluff-pulp layers, each having a surface weight of 350 g/m², and an intermediate layer of 4.8 g superabsorbent of high gel-strength.

The upper absorbent layer of the body B had a surface weight of 400 g/m² and contained 1.2 g superabsorbent of the same type used in body A. This superabsorbent was mixed generally homogeneously with the fluff-pulp fibres. The lower absorbent layer of body B had a surface weight of 700 g/m² and contained 4.8 g superabsorbent of the same type used in body A. The superabsorbent was mixed generally homogeneously with the fluff-pulp fibres.

The test bodies were compressed to a bulk of 7 cm³/g.

Tests were also carried out on two other fluff-pulp bodies C and D which were constructed in a manner corresponding to bodies A and B, but with the difference that the fluff-pulp in the lower absorbent layer also comprised CTMP softwood pulp.

3*28 ml of sample liquid (0.9% NaCl solution) were poured onto the wetting point through a pipe at intervals of 20 and 40 minutes respectively. Filter paper was placed over the wetting point and loaded with a weight of 1.1 kg (2.8 kPa) for 15 seconds. The filter papers were weighed before and after being subjected to load and rewetting was recorded.

The results are shown in the following Table 1.

TABLE 1

| Sample (g) body | Pulp upper/ lower core | Superabsorbent applied in upper/ lower core | Rewetting |
|---|---|---|---|
| A | CTMP/CP | mix/layer | 1.3 |
| B | CTMP/CP | mix/mix | 1.5 |
| C | CTMP/CTMP | mix/layer | 5.1 |
| D | CTMP/CTMP | mix/mix | 9.4 |

EXAMPLE 2

A comparison test was also carried out with respect to the second absorbent layer 17. This comparison was made between test bodies in which pulp fibres and superabsorbent particles were mixed essentially homogeneously with one another and in which the superabsorbent particles were applied in a layer as described in the aforegoing in accordance with the invention. The test bodies weighed 14 g, excluding superabsorbent. The pulp used was a chemical softwood pulp and the superabsorbent was of the kind which exhibits a high gel-strength. All test bodies had a bulk of 12 cm$^3$/g.

Instantaneous absorption, rewetting, horizontal liquid dispersion and coherency were measured in respect of test bodies that contained 10 or 30% superabsorbent either mixed essentially homogeneously in the pulp or placed in layers.

The analyses were carried out in the following manner.

Instantaneous Absorption

Four quantities of liquid (0.9% NaCl solution), each of 28 ml, were delivered to the bodies at 20-minute intervals. The time taken for all liquid to be absorbed was measured (visual observation). The results obtained after the last delivery are shown in Table 2.

TABLE 2

| Superabsorbent (%) | Mix/Layer | Instantaneous Abs. (s) |
|---|---|---|
| 0 | — | 34.0 |
| 10 | mix | 10.1 |
| 10 | layer | 7.1 |
| 30 | mix | 7.5 |
| 30 | layer | 5.5 |

Rewetting

Rewetting tests were carried out in respect of test bodies corresponding to the test bodies used in the instantaneous absorption test. The tests were carried out in a manner corresponding to the method applied in the rewetting test described in Example 1. The results are shown in Table 3.

TABLE 3

| Superabsorbent (%) | Mix/Layer | Rewetting (g) |
|---|---|---|
| 0 | — | 11.4 |
| 10 | mix | 9.3 |
| 10 | layer | 4.7 |
| 30 | mix | 2.7 |
| 30 | layer | 2.8 |

These results show that with 10% superabsorbents, a much lower rewetting tendency is obtained with the superabsorbents placed in layers in comparison with superabsorbents that are mixed with the pulp fibres. With 30% superabsorbents, the result obtained with layered superabsorbents was essentially the same as that obtained with superabsorbents that were mixed with the pulp fibres.

Horizontal Dispersion

The dispersion test was carried out with test bodies that corresponded to the above-mentioned. The test were carried out in the following manner: 3*28 ml test liquid (0.9% NaCl solution) were poured through a pipe onto the wetting point at 20-minute intervals. The horizontal dispersion was measured in cm after 60 min. from the time of the first addition.

The results are shown in the following Table 4.

TABLE 4

| Superabsorbent (%) | Mix/Layer | Horizontal Dispersion (cm) |
|---|---|---|
| 0 | — | 28 |
| 10 | mix | 23.3 |
| 10 | layer | 27.5 |
| 30 | mix | 12.5 |
| 30 | layer | 19.3 |

The results show a high liquid dispersion in those test bodies in which the superabsorbents were laid in layers in comparison with the test bodies in which the superabsorbents were mixed with the pulp fibres. This enables the liquid to reach a large proportion of the superabsorbent particles distributed in the absorbent body.

Retentiveness

The retentiveness of test bodies corresponding to those used in the above tests was measured, i.e. the amount of liquid that respective test bodies were able to retain when subjected to load. The tests were carried out in the following manner: The test bodies were weighed and then submerged in test liquid for 5 minutes, after which they were removed from the liquid. The test bodies were then subjected to a load of 10 kPa for 1 minute and then weighed. The liquid retentiveness of the bodies was determined as: $(m_2-m_1)/m_1$ (g/g), where $m_1$=pulp dry test
$m_2$=pulp wet test The results are shown in Table 5.

TABLE 5

| Superabsorbent (%) | Mix/Layer | Retentiveness /g/g) |
|---|---|---|
| 0 | — | 7.2 |
| 10 | mix | 8.8 |
| 10 | layer | 9.1 |
| 30 | mix | 11.8 |
| 30 | layer | 13.4 |

The results show a higher degree of retentiveness in those test bodies in which the superabsorbents were present in layers than those test bodies in which the superabsorbents were mixed with the pulp fibres.

In summary, it can be established that the tests carried out show improved absorption properties in respect of test bodies corresponding to the inventive second absorbent layer in which the superabsorbents were placed in a layer between layers of pulp fibres. In combination with an upper absorbent layer having an open fibre structure and low liquid dispersion ability and which therewith is able to receive large quantities of liquid over a short period of time, an absorbent body which possesses very good absorption properties has been produced in accordance with the invention.

We claim:

1. An absorbent body, comprising:
   a first fibre-based absorbent layer of fluff pulp which is intended to lie proximal to a wearer in use,
   a second fibre-based absorbent layer of fluff pulp which is intended to lie distal to the wearer in use,
   the second absorbent layer exhibiting a high liquid-dispersing ability,
   the first absorbent layer includes a superabsorbent material of high gel-strength which is admixed essentially uniformly in fibre material of the first layer within at least one area of the first layer, said first absorbent layer containing between 2 and 30% superabsorbent material calculated on the total dry weight of the layer in the at least one area in which the superabsorbent is admixed, and
   the second absorbent layer includes upper and lower layers of fibre-based fluff-pulp material and at least one layer of superabsorbent material disposed between the upper and lower fibre layers within at least one area of the second layer, the second absorbent layer containing between 2 and 60% superabsorbent material calculated on the total dry weight of the layer in the at least one area in which the superabsorbent material is distributed, and wherein the at least one layer of superabsorbent material is substantially not mixed with the upper and lower layers of fibre-based material.

2. The absorbent body according to claim 1, wherein the first absorbent layer has a low liquid-dispersing ability.

3. The absorbent body according to claim 2, wherein the superabsorbent material in the second absorbent layer has high gel strength.

4. The absorbent body according to claim 2, wherein a major part of the fibre material in the first absorbent layer includes a fluff-pulp having an open fibre structure and a critical bulk above 8 cm$^3$/g at 2.5 kPa; and fibre material in the second absorbent layer in at least the upper fibre layer of said second absorbent layer lying proximal to the first absorbent layer includes mainly another type of fluff-pulp having a critical bulk beneath 8 cm$^3$/g at 2.5 kPa and has a higher liquid-dispersing ability than the fluff-pulp in the first absorbent layer.

5. The absorbent body according to claim 1 wherein the superabsorbent material in the second absorbent layer has high gel-strength.

6. The absorbent body according to claim 5, wherein a major part of the fibre material in the first absorbent layer includes a fluff-pulp having an open fibre structure and a critical bulk above 8 cm$^3$/g at 2.5 kPa; and fibre material in the second absorbent layer in at least the upper fibre layer of said second absorbent layer lying proximal to the first absorbent layer includes mainly another type of fluff-pulp having a critical bulk beneath 8 cm$^3$/g at 2.5 kPa and has a higher liquid-dispersing ability than the fluff-pulp in the first absorbent layer.

7. The absorbent body according to claim 1, wherein the first absorbent contains between 2 and 15% superabsorbent material calculated on the total dry weight of the layer.

8. The absorbent body according to claim 1, wherein the proportion of superabsorbent material in the second absorbent layer is between 10 and 50% calculated on the total dry weight of the layer in the area or areas of the absorbent first layer in which the superabsorbent material is distributed.

9. The absorbent body according to claim 1, wherein the first fibre-based absorbent layer is fixed directly to the second fibre-based absorbent layer.

10. A diaper, comprising:
    a casing;
    an absorbent body enclosed in the casing,
    a back part which is intended to be placed rearwardly on a wearer in use,
    a front part which is intended to be placed forwardly on the wearer in use, and
    a crotch part which extends between the back part and the front part and which is intended to be placed in the crotch region of the wearer in use, between the thighs thereof, as seen from a side of the diaper proximal to the wearer in use,
    the absorbent body includes a first fibre-based absorbent layer of fluff-pulp and a second fibre-based absorbent layer of superabsorbent material and fibre-based fluff-pulp material, which second absorbent layer exhibits a high liquid-dispersing ability,
    the first absorbent layer includes a superabsorbent material of high gel strength mixed essentially uniformly in the fibre material within at least one area of the layer, said first absorbent layer containing between 2 and 30% superabsorbent material calculated on the total dry weight of the layer in the at least one area in which the superabsorbent is mixed, and
    the second absorbent layer includes at least one layer of superabsorbent material within at least one area of the second layer, the second absorbent layer containing between 2 and 60% superabsorbent material calculated on the total dry weight of the layer in the at least one area in which the superabsorbent material is distributed, and,
    wherein the at least one layer of superabsorbent material of the second absorbent layer is substantially not mixed with the fibre-based material of the second absorbent layer.

11. The diaper according to claim 10, wherein the first absorbent layer extends over only a part of a surface area of the second absorbent layer wherein the first absorbent layer is located essentially in the crotch part of the diaper.

12. The diaper according to claim 10, wherein the first absorbent layer contains between 2 and 15% superabsorbent material calculated on the total dry weight of the layer.

13. The diaper according to claim 8, wherein the proportion is between 10 and 50%.

14. The diaper according to claim 10, wherein the second absorbent layer includes the one layer of superabsorbent material being disposed between an upper fibre layer and a lower fibre layer.

15. The diaper according to claim 14, wherein the first fibre-based absorbent layer is fixed directly to the second fibre-based absorbent layer.

16. The diaper according to claim 10, wherein the first fibre-based absorbent layer is fixed directly to the second fibre-based absorbent layer.

17. An absorbent body comprising:
    a first fibre-based absorbent layer which is intended to lie proximal to a wearer in use,
    a second fibre-based absorbent layer which is intended to lie distal to the wearer in use,
    the second absorbent layer exhibiting a high liquid-dispersing ability,
    the first absorbent layer includes a superabsorbent material of high gel-strength which is admixed essentially uniformly in fibre material of the first absorbent layer within a least one area of the first absorbent layer, and the second absorbent layer includes upper and lower fibre layers and at least one layer of superabsorbent material disposed between the upper and lower fibre layers;

wherein a major part of the fibre material in the first absorbent layer includes a fluff-pulp having an open fibre structure and a critical bulk above 8 cm$^3$/g at 2.5 kPa; and fibre material in at least the upper fibre layer of said second absorbent layer lying proximal to the first absorbent layer includes mainly another type of fluff-pulp having a critical bulk beneath 8 cm$^3$/g at 2.5 kPa and has a higher liquid-dispersing ability than the fluff-pulp in the first absorbent layer.

18. The absorbent body according to claim 17, wherein the fluff-pulp of the first absorbent layer has a fibre weight between 180 and 600 mg/km; and the fluff-pulp of the upper fiber layer of the second absorbent layer has a fibre weight between 140 and 190 mg/km.

19. The absorbent body according to claim 18, wherein the first absorbent layer is comprised mainly of a chemi-thermo mechanical fluff-pulp; and at least 60% of the upper fiber layer of the second absorbent layer is comprised of a chemical fluff-pulp.

20. The absorbent body according to claim 17, wherein the first absorbent layer contains between 2 and 30% superabsorbent material calculated on the total dry weight of the layer.

* * * * *